United States Patent [19]

Engelhardt et al.

[11] Patent Number: 5,502,231

[45] Date of Patent: Mar. 26, 1996

[54] PROCESS FOR THE PREPARATION OF CYCLIC VINYLPHOSPHONIC ESTERS

[75] Inventors: Fritz Engelhardt; Ulrich Riegel, both of Frankfurt am Main; Hans-Jerg Kleiner, Kronberg, all of Germany

[73] Assignee: Cassella Aktiengesellschaft, Germany

[21] Appl. No.: 391,528

[22] Filed: Feb. 21, 1995

[30] Foreign Application Priority Data

Mar. 4, 1994 [DE] Germany .......................... 44 07 272.4

[51] Int. Cl.[6] ................................................. C07F 9/6564
[52] U.S. Cl. ................. 558/110; 558/77; 558/83
[58] Field of Search .................. 558/110, 83, 77

[56] References Cited

U.S. PATENT DOCUMENTS

| | | | |
|---|---|---|---|
| 3,887,656 | 6/1975 | Shim | 260/937 |
| 3,984,502 | 10/1976 | Shim | 260/986 |
| 4,093,588 | 6/1978 | Spivak et al. | 260/45.8 R |
| 4,959,441 | 9/1990 | Engelhardt et al. | 558/161 |
| 4,977,066 | 12/1990 | Gersdorf et al. | 430/277 |
| 5,066,745 | 11/1991 | Engelhardt et al. | 526/240 |

FOREIGN PATENT DOCUMENTS 2083042  3/1982  United Kingdom .

OTHER PUBLICATIONS

*Soviet Inventions Illustrated:* 283214, p. 19, Jun. 1971 Derwent Publications Ltd., London, GB.

*Primary Examiner*—Johann Richter
*Assistant Examiner*—Laura R. Cross
*Attorney, Agent, or Firm*—Connolly & Hutz

[57] ABSTRACT

The present invention relates to a process for the preparation of compounds of the general formula I

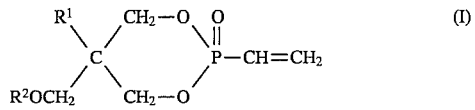

in which $R^1$ and $R^2$ are defined as stated in claim 1, characterized in that a 1,1,1-tris(hydroxymethyl)-($C_2$–$C_5$)-alkane or 2,2-bis(hydroxymethyl)-1,3-propanediol is reacted with vinylphosphonic anhydride.

13 Claims, No Drawings

PROCESS FOR THE PREPARATION OF CYCLIC VINYLPHOSPHONIC ESTERS

The present invention relates to a process for the preparation of cyclic vinylphosphonic esters using vinylphosphonic anhydride.

Cyclic vinylphosphonic esters are already known and are described in EP-A 343 427. Representatives of this class of substances, which contain at least two double bonds, can be employed as crosslinking agents in the preparation of polymers, in particular of water-swellable hydrogels, from unsaturated, hydrophilic monomers. Compounds having only one double bond are precursors of the compounds having two double bonds.

The synthesis which is described in EP-A 343 427, from 1,1,1-tris(hydroxymethyl)alkanes and/or 2,2-bis-(hydroxymethyl)-1,3-propanediol and vinylphosphonyl dichloride using bases as acid scavengers, is disadvantageous in that it requires the bases to be recycled by decomposition of the salts produced, using water-soluble organic bases. However, this results in the production of salt-containing effluents.

There is therefore a need for a more advantageous preparation process.

The present invention relates to a process for the preparation of compounds of the general formula I $$\begin{array}{c} R^1 \quad CH_2-O \quad O \\ \diagdown \diagup \quad \diagdown \parallel \\ C \quad P-CH=CH_2 \\ \diagup \diagdown \quad \diagup \\ R^2OCH_2 \quad CH_2-O \end{array}$$ (I)

in which
$R^1$ is $(C_1-C_4)$-alkyl or $-CH_2OR^3$;
$R^2$, if $R^1$ is $(C_1-C_4)$-alkyl, is hydrogen or $$\begin{array}{c} O \\ \parallel \\ -P-CH=CH_2 \\ | \\ OH \end{array}$$

and, if $R^1$ is $-CH_2OR^3$, $R^2$ forms together with $R^3$ a group $$\begin{array}{c} O \\ \parallel \\ -P-CH=CH_2, \\ | \end{array}$$

characterized in that a 1,1,1-tris (hydroxymethyl)-$(C_2-C_5)$-alkane or 2,2-bis(hydroxymethyl)-1,3-propanediol is reacted with vinylphosphonic anhydride.

$R^1$ as $(C_1-C_4)$-alkyl may be straight-chain or branched and is, for example, methyl, ethyl, n-propyl, isopropyl, n-butyl, sec-butyl, isobutyl or tert-butyl.

In the general formula I, $R^1$ is preferably ethyl and $R^2$ is hydrogen or $$\begin{array}{c} O \\ \parallel \\ -P-CH=CH_2. \\ | \\ OH \end{array}$$

Furthermore, it is preferred for $R^1$ to be $-CH_2OR^3$ and for $R^2$ together with $R^3$ to form a group $$\begin{array}{c} O \\ \parallel \\ -P-CH=CH_2. \\ | \end{array}$$

The process according to the invention is consequently employed preferably for the preparation of the compounds of the formula Ia $$\begin{array}{c} CH_3 \\ | \\ CH_2 \quad CH_2-O \quad O \\ \diagdown \diagup \quad \diagdown \parallel \\ C \quad P-CH=CH_2, \\ \diagup \diagdown \quad \diagup \\ HOCH_2 \quad CH_2-O \end{array}$$ (Ia)

of the formula Ib $$\begin{array}{c} CH_3 \\ | \\ CH_2 \quad CH_2-O \quad O \\ \diagdown \diagup \quad \diagdown \parallel \\ O \quad C \quad P-CH=CH_2 \\ \parallel \diagup \diagdown \diagup \\ H_2C=CH-P-OCH_2 \quad CH_2-O \\ | \\ OH \end{array}$$ (Ib)

and of the formula Ic $$\begin{array}{c} O \quad O-CH_2 \quad CH_2-O \quad O \\ \parallel \diagup \quad \diagdown \diagup \quad \diagdown \parallel \\ H_2C=CH-P \quad C \quad P-CH=CH_2. \\ \diagdown \quad \diagup \diagdown \diagup \\ O-CH_2 \quad CH_2-O \end{array}$$ (Ic)

In the process according to the invention the molar ratios of the reactants are advantageously chosen in dependence on the compound to be prepared. For example, for the preparation of the compound of the formula Ia, 1,1,1-tris(hydroxymethyl)propane is reacted with vinylphosphonic anhydride preferably in a molar ratio of 1:2, but for the preparation of the compound of the formula Ib these reactants are preferably reacted in a molar ratio of 1:3. For the preparation of the compound of the formula Ic, 2,2-bis(hydroxymethyl)-1,3-propanediol is reacted with vinylphosphonic anhydride in a molar ratio which is preferably 1:3 and particularly preferably 1:4. In specific instances, however, molar ratios even higher than those indicated are possible.

The process according to the invention can be carried out with or without the use of a solvent. If a solvent is to be used, suitable examples thereof are dimethylformamide, acetonitrile, ethyl acetate or dichloromethane.

The process according to the invention is generally carried out at temperatures of from −10° C. to 150° C. Temperatures of from 30° to 80° C. are preferred.

It may be advantageous to carry out the process according to the invention in the presence of a polymerization inhibitor. Examples of suitable polymerization inhibitors are hydroquinone, hydroquinone monomethyl ether and phenothiazine.

Initially, the process according to the invention always leads to a reaction mixture containing not only a compound of the general formula I but also significant quantities of vinylphosphonic acid, which has been formed from the anhydride. However, this can be separated off by appropriate methods which are known per se.

If the compound of the general formula I which has been prepared is to be used as crosslinking agent in the preparation of hydrogels, then it is not necessary to separate off the vinyl phosphonic acid, and the reaction mixture can be employed directly as obtained.

1,1,1-Tris(hydroxymethyl)alkanes, 2,2-bis(hydroxymethyl)- 1,3-propanediol and vinylphosphonic anhydride are inexpensive compounds which are commercially available or can be prepared by known methods.

EXAMPLE 1

496 g (3.7 mol) of 1,1,1-tris(hydroxymethyl)propane are dissolved in 740 g of dichloromethane, and 2000 g of a 50% strength solution of vinylphosphonic anhydride in dichloromethane (11.11 mol) are added dropwise thereto at 30° C. over 2 h, with vigorous stirring. The mixture is then maintained at reflux for 30 h. The resulting reaction solution is allowed to cool and then filtering aid is added, and the solution is stirred and filtered with suction. The filtrate is freed from the dichloromethane in vacuo, to give about 1400 g of an oily reaction mixture which is composed, according to measurement by $^{31}$P-NMR, of the following principal components: 9.5% of the compound Ia, 44.5% of the compound Ib, 43.5% of vinylphosphonic acid.

EXAMPLE 2

675 g (7.5 mol) of vinylphosphonic anhydride are heated to 40° C., and 335.2 g (2.5 mol) of 1,1,1-tris(hydroxymethyl)propane are introduced in portions with vigorous stirring. The temperature rises to from 60° to 70° C. and is maintained with cooling. The reaction mixture is then stirred at from 45° to 50° C. for 24 h before 1 g of hydroquinone monomethyl ether is added and the mixture is cooled, to give 1011 g of an oily reaction mixture which is composed, according to measurement by $^{31}$P-NMR, of the following principal components: 5% of the compound Ia, 45% of the compound Ib, 45% of vinylphosphonic acid.

EXAMPLE 3

1000 g (11.11 mol) of vinylphosphonic anhydride are heated to 53° C., and 378 g (2.78 mol) of 2,2-bis(hydroxymethyl)- 1,3-propanediol are added in portions with vigorous stirring, and the temperature rises to 80° C. The mixture is subsequently stirred at 50° C. for about 24 h and then cooled, and isopropanol is added. After stirring has been continued for several hours the mixture is filtered with suction and the product is washed with acetone, to give 340 g of the compound Ic having a melting point of from 157° to 159° C. This corresponds to a yield of 44% of theory.

We claim:

1. Process for the preparation of compounds of the formula I $$\underset{R^2OCH_2}{\overset{R^1}{>}}C\underset{CH_2-O}{\overset{CH_2-O}{<}}\overset{O}{\underset{\|}{P}}-CH=CH_2 \quad (I)$$

in which

R$^1$ is (C$_1$–C$_4$)-alkyl or —CH$_2$OR$^3$;

R$^2$, if R$^1$ is (C$_1$–C$_4$)-alkyl, is hydrogen or $$\begin{array}{c} O \\ \| \\ -P-CH=CH_2 \quad \text{and,} \\ | \\ OH \end{array}$$

if R$^1$ is —CH$_2$OR$^3$, R$^2$ forms together with R$^3$ a group $$\begin{array}{c} O \\ \| \\ -P-CH=CH_2, \\ | \end{array}$$

comprising the reaction of a 1,1,1-tris(hydroxymethyl)-(C$_2$–C$_5$)-alkane or 2,2-bis(hydroxymethyl)- 1,3-propanediol with vinylphosphonic anhydride.

2. The process according to claim 1, wherein R$^1$ is ethyl and R$^2$ is hydrogen or $$\begin{array}{c} O \\ \| \\ -P-CH=CH_2. \\ | \\ OH \end{array}$$

3. The process according to claim 1, wherein that R$^1$ is —CH$_2$OR$^3$ and R$^2$ forms together with R$^3$ a group $$\begin{array}{c} O \\ \| \\ -P-CH=CH_2. \\ | \end{array}$$

4. The process according to claim 1, wherein said reaction is carried out without the presence of a solvent.

5. The process according to claim 1, wherein said reaction is carried out in the presence of a solvent.

6. The process according to claim 5, wherein said solvent is dimethylformamide, acetonitrile, ethyl acetate or dichloromethane.

7. The process according to claim 1 wherein said reaction is carried out in the presence of a polymerization inhibitor.

8. The process according to claim 7, wherein said polymerization inhibitor is hydroquinone, hydroquinone monomethyl ether or phenothiazine.

9. The process according to claim 1, wherein the compound of formula I is $$\underset{HOCH_2}{\overset{CH_3}{\underset{|}{CH_2}}}\underset{CH_2-O}{>}C\underset{CH_2-O}{\overset{CH_2-O}{<}}\overset{O}{\underset{\|}{P}}-CH=CH_2. \quad (Ia)$$

10. The process according to claim 1, wherein the compound of formula I is $$\underset{\underset{OH}{\overset{\|}{\underset{|}{P}}}-OCH_2}{\overset{CH_3}{\underset{|}{CH_2}}}C\underset{CH_2-O}{\overset{CH_2-O}{<}}\overset{O}{\underset{\|}{P}}-CH=CH_2. \quad (Ib)$$
$$H_2C=CH$$

11. The process according to claim 1, wherein the compound of formula I is $$H_2C=CH-\underset{\underset{O-CH_2}{\overset{\|}{\underset{}{P}}}}{\overset{O}{\underset{}{P}}}\underset{O-CH_2}{\overset{O-CH_2}{<}}C\underset{CH_2-O}{\overset{CH_2-O}{<}}\overset{O}{\underset{\|}{P}}-CH=CH_2. \quad (Ic)$$

12. The process according to claim 1, wherein the reaction is carried out at a temperature range from about −10° C. to about 150° C.

13. The process according to claim 1, wherein the reaction is carried out at a temperature range from about 30° C. to about 80° C.

* * * * *